(12) United States Patent
Howieson

(10) Patent No.: US 8,339,606 B2
(45) Date of Patent: Dec. 25, 2012

(54) PORTAL

(75) Inventor: Iain Howieson, Stirling (GB)

(73) Assignee: Cascade Technologies Limited, Stirling (GB)

( * ) Notice: Subject to any disclaimer, the term of this patent is extended or adjusted under 35 U.S.C. 154(b) by 328 days.

(21) Appl. No.: 12/516,947

(22) PCT Filed: Nov. 12, 2007

(86) PCT No.: PCT/GB2007/004333
§ 371 (c)(1),
(2), (4) Date: May 29, 2009

(87) PCT Pub. No.: WO2008/065338
PCT Pub. Date: Jun. 5, 2008

(65) Prior Publication Data
US 2010/0067014 A1    Mar. 18, 2010

(30) Foreign Application Priority Data
Nov. 29, 2006    (GB) .................................. 0623812.5

(51) Int. Cl.
*G01N 21/00* (2006.01)
(52) U.S. Cl. ........................................ 356/432; 356/434
(58) Field of Classification Search .................... None
See application file for complete search history.

(56) References Cited

U.S. PATENT DOCUMENTS

| | | | | |
|---|---|---|---|---|
| 4,987,767 A * | 1/1991 | Corrigan et al. | ............. | 73/23.36 |
| 5,094,533 A * | 3/1992 | Sawada et al. | ................ | 356/338 |
| 6,040,191 A * | 3/2000 | Grow | ............................... | 506/12 |
| 6,610,977 B2 * | 8/2003 | Megerle | ......................... | 250/287 |
| 6,840,122 B1 * | 1/2005 | Jenkins et al. | ............. | 73/864.33 |
| 7,401,498 B2 * | 7/2008 | Syage et al. | ................. | 73/28.01 |
| 7,583,710 B2 * | 9/2009 | Dantus et al. | .................... | 372/25 |
| 2003/0085348 A1 * | 5/2003 | Megerle | ......................... | 250/287 |
| 2004/0124376 A1 | 7/2004 | Ershov et al. | | |
| 2005/0052948 A1 | 3/2005 | Caulfield et al. | | |
| 2005/0157303 A1 * | 7/2005 | Langford et al. | ............. | 356/437 |
| 2005/0230604 A1 * | 10/2005 | Rowe et al. | .................... | 250/221 |
| 2008/0053252 A1 * | 3/2008 | Jenkins et al. | ............. | 73/864.33 |
| 2010/0245081 A1 * | 9/2010 | Arcaini et al. | ................ | 340/540 |
| 2010/0282960 A1 * | 11/2010 | Clark | ........................... | 250/282 |

FOREIGN PATENT DOCUMENTS

| WO | WO99/21148 | 4/1999 |
|---|---|---|
| WO | WO03087787 A1 | 10/2003 |
| WO | WO2006/090353 A1 | 8/2006 |

OTHER PUBLICATIONS

"Explosives detection personnel portals" (online), Sep. 28, 2005, XP002467031, http://www.sandia.gov/mission/homeland/factsheets/archive/personnel.portals_2004_4153P.pdf.
International Search Report for PCT/GB2007/004333, dated Feb. 14, 2008.

* cited by examiner

*Primary Examiner* — Gordon Stock, Jr.
(74) *Attorney, Agent, or Firm* — Moore & Van Allen, PLLC; W. Kevin Ransom

(57) ABSTRACT

A portal or gateway that includes a detector comprising a chirped laser; an open optical sample cell and a detector for detecting light from the chirped laser that has passed through the cell. The chirped laser may be a quantum cascade laser.

18 Claims, 2 Drawing Sheets

PORTAL

FIELD OF THE INVENTION

The present invention relates to a portal or gateway that is adapted to detect materials, in particular hazardous or undesirable materials.

BACKGROUND OF THE INVENTION

Security is a growing problem in many environments, for example, airports. With the threat of terrorism on the rise, it is becoming increasingly important to be able to detect potentially hazardous materials, particularly those being carried through airport security gates. In practice, however, this is difficult because often only trace levels of the materials are present and many existing systems do not have the sensitivity to detect such low levels.

One known system for detecting hazardous materials in an airport environment uses Ion Mobility Spectroscopy (IMS). Particles are collected from a sample region, typically a security gate and transported via air currents or a sample line to a sample collection chamber. This is done until a sample of a pre-determined concentration is collected. Once the pre-concentrated sample is collected, the particles are then heated until they reach the gas phase and are subsequently ionized so that their mass can be determined via a measure of the time of flight between two charged plates. The molecular mass provides an indication of the identity of particles collected.

A problem with IMS is that many different molecules are found to have similar masses making this susceptible to both false positive and false negative identification. A further problem is that the sample area over which the particles are collected is relatively limited, leaving the possibility of particles of interest not being captured. In addition, the sample has to be pre-concentrated, heated and ionized which means that the measurement response time is typically of the order of tens of seconds. This is too slow for many security applications.

SUMMARY OF THE INVENTION

According to the present invention, there is provided a portal or gateway that includes a gas detector comprising a chirped laser; an open optical sample cell and a detector for detecting light from the chirped laser that has passed through the cell, preferably multiple times. Preferably, the open optical sample cell is non-resonant.

The open sample cell may extend along substantially the full length of the portal. The open sample cell may be longer than 1 meter, and ideally longer than 1.5 meters.

The wavelength variation provided by the wavelength chirp itself is used to provide a wavelength scan. Hence, there is no need to tune the effective emission linewidth across a spectral region using, for example, a slow DC current ramp superimposed on the pulse train. This means that the sampling rate can be very high and a full spectral analysis can be done very quickly. Using fast chirps means that the effects of turbulence and vibration noise can be overcome. This is a significant advantage.

The chirped laser may be a semiconductor laser, for example a semiconductor diode laser. The chirped light is generated by applying a one or a series of substantially step function electrical pulses to the semiconductor diode laser to cause the laser to output one or more pulses, each having a continuous wavelength chirp, for injecting into the optical cell. The laser may be a quantum cascade laser.

Each applied pulse may have a duration that is greater than 150 ns, in particular greater than 200 ns. Each applied pulse may have a duration that is in the range of 150 to 300 ns, preferably 200 to 300 ns. This can provide a tuning range of about 60 GHz.

The chirp rate may be selected so that there is a time delay between spots on the reflecting elements of the non-resonant cell sufficient to substantially prevent light interference from occurring, wherein the spots define locations at which the injected chirp is reflected from the cell walls.

Each detected pulse may have a duration that is greater than 150 ns, in particular greater than 200 ns. Preferably, each detected pulse has a duration that is in the range of 150 to 300 ns, preferably 200 to 300 ns.

BRIEF DESCRIPTION OF THE DRAWINGS

Various aspects of the invention will now be described by way of example only and with reference to the following drawings, of which.

DETAILED DESCRIPTION OF THE DRAWINGS

Figure 1:
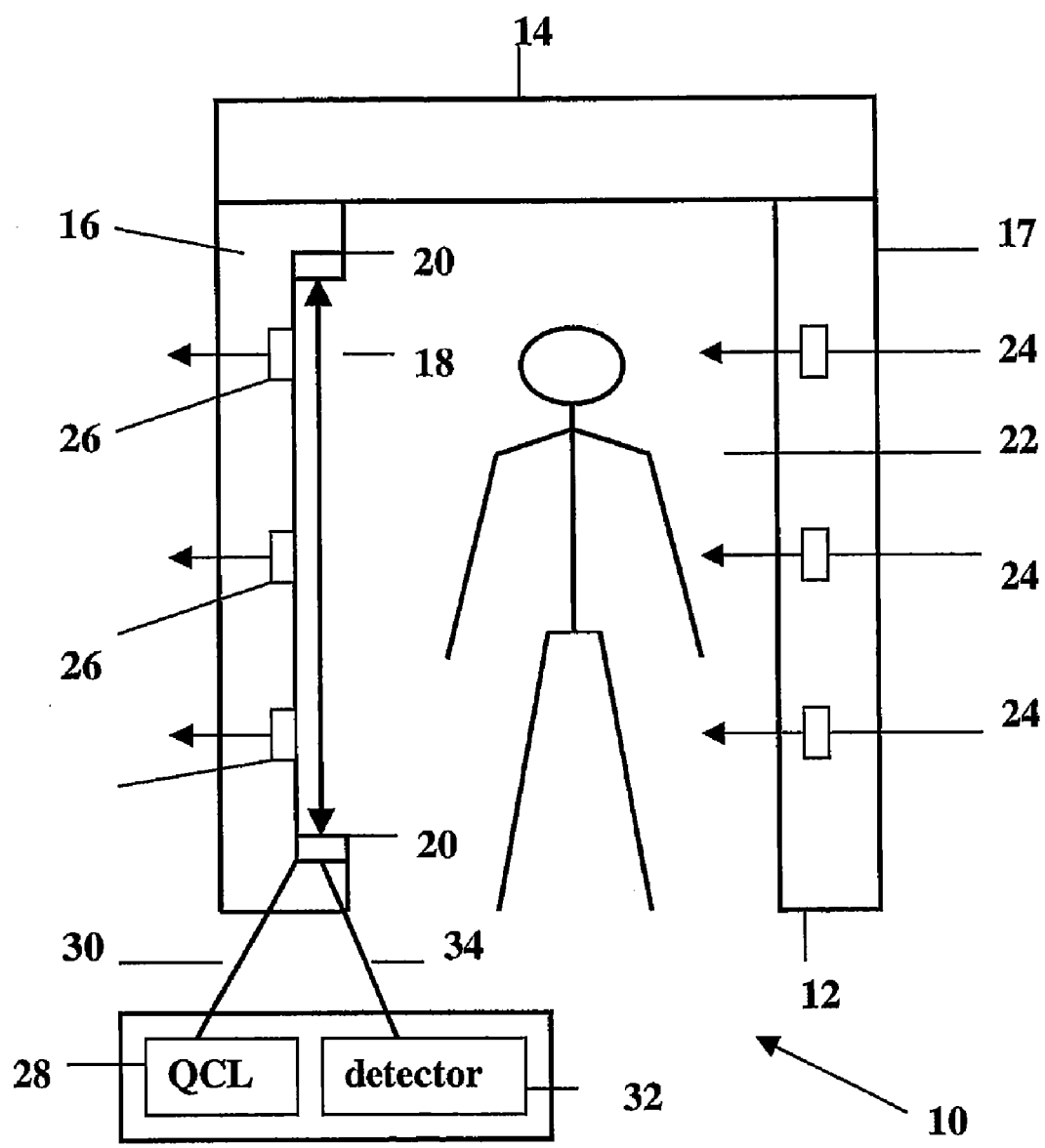
FIG. 1 is a schematic diagram of a single portal.

FIG. 1 shows a portal or gateway 10 through which a person has to pass to enter a secure or controlled area in, for example, an airport. This has an open aluminum framework 12 with an upper horizontal lintel 14 and two opposing vertical supports 16 and 17. Within one of the vertical supports 16 is an open, non-resonant optical sample cell 18, each end of which is defined by a mirror 20. By open it is meant that there is no physical barrier between the optical cell 18 and the portal opening 22. In order to ensure that as many molecules as possible enter the cell 18 without adsorption losses, the laser cell 18 extends along the entire vertical extent of the support 16. Hence, in practice, preferably the open sample cell 18 is longer than 1 meter, and ideally longer than 1.5 meters.

The use of an entirely open and relatively long optical cell 18 is a key advantage when detecting low gas concentrations, for example parts per billion. Were gas pumped into a closed cell, molecules would stick to the cell walls, and may be detectable for a long period after the cell has been refreshed. This could create false positives and reduce response time. To avoid this problem, the entire cell could be heated. However, this is not necessary using the open framework of the present invention, as the long length and open configuration prevent sticking and provide very quick cell refresh rates and far faster measurement times.

On the support 17 opposite the sample cell 18 is provided a series of fans 24 arranged to blow air substantially horizontally towards the sample cell 18. This ensures that the general direction of airflow is into the sample cell 18. Optionally fans 26 may be provided on the sample cell support 16 to draw air towards it, thereby augmenting the pull on molecules into the cell 18. These fans 26 also help speed up the refresh rate of the cell.

Light from a quantum cascade laser 28 is coupled into the cell using a fiber optic cable 30. A step function electrical pulse is applied to the quantum cascade laser 28 to cause it to output a continuous wavelength chirp. Preferably, each applied pulse has a duration that is greater than 150 ns, in particular greater than 200 ns. Preferably, each applied pulse has a duration that is in the range of 150 to 300 ns, preferably 200 to 300 ns. This can provide a tuning range of about 60 GHz.

The continuous wavelength chirp is injected into the optical cell 18 via the optical fiber coupling 30. The wavelength variation provided by this is used as an intra-pulse scan. The chirp rate is selected to substantially prevent light interference occurring in the optical cell. In particular, the chirp rate may be selected so that there is a time delay between spots on the reflecting elements of the non-resonant cell sufficient to substantially prevent light interference from occurring, wherein the spots define locations at which the injected chirp is reflected from the cell walls. This ensures that operation of the detector is fringe free. Techniques for doing this are described in WO03087787, the contents of which are incorporated herein by reference.

Light injected into the cell 18 undergoes multiple passes. In order to provide a high level of sensitivity, preferably the cell 18 is arranged to provide 100 or more passes. Light emitted from the cell 18 is coupled to a detector 32 using a fiber optic cable 34. The wavelength variation of the applied chirped pulses is sufficient to allow the chemical fingerprints of certain materials to be detected, for example peroxide and EGDN. In this way, the detected light can be used to unambiguously identify certain chemicals, in particular some hazardous or undesirable materials, by for example comparing the detected fingerprint with stored fingerprints for known materials. Whilst ideally a positive identification of a chemical is achieved, optionally, unexplained signals could be used to give low level alerts.

Using a quantum cascade laser in this arrangement provides numerous advantages. Because of its very rapid response rate, the measurement time can be significantly reduced compared to other arrangements. Also, because the sample cell 18 is completely open, no losses are incurred through transport lines or other types of sample collection arrangement. In addition, the overall measurement is significantly more sensitive than other conventional measurements.

Figure 2:
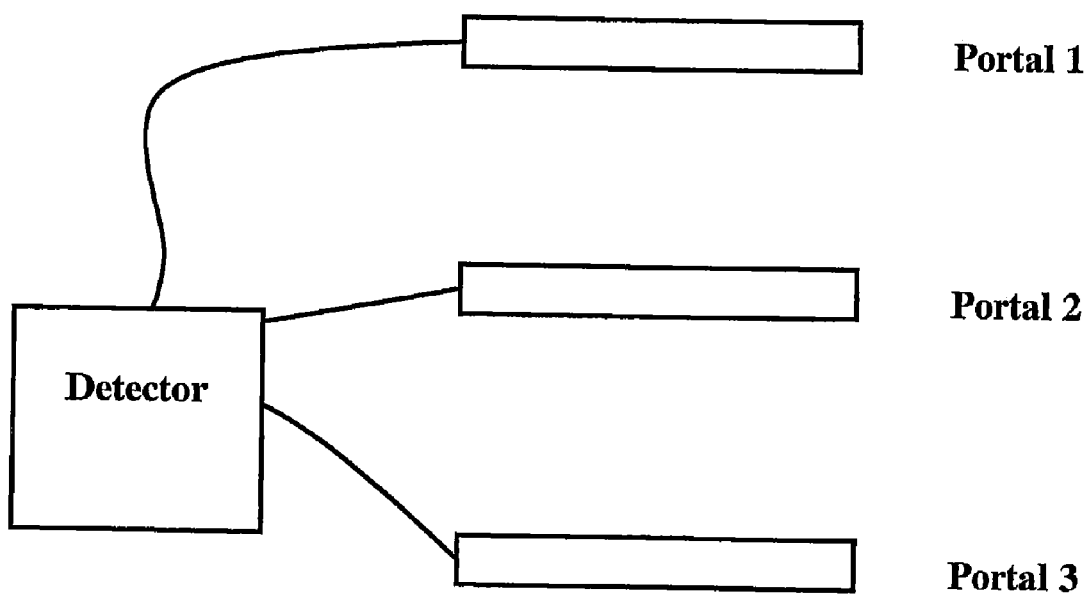
FIG. 2 is a schematic diagram of a multiple portal arrangement.

A skilled person will appreciate that variations of the enclosed arrangement are possible without departing from the invention. For example, whilst the invention has been described in terms of a portal for a person to walk through, it could equally be a portal or opening or gateway through which goods have to pass before, for example, entering a secure or controlled area. Equally, although FIG. 1 shows a single portal, a plurality of these could be provided, with their outputs fed to a single detector unit, as shown in FIG. 2. Accordingly, the above description of the specific embodiment is made by way of example only and not for the purposes of limitations. It will be clear to the skilled person that minor modifications may be made without significant changes to the operation described.

The invention claimed is:

1. A portal or gateway configured to allow people or items to pass through, wherein the portal or gateway comprises:
    a vertical support;
    a chirped laser;
    an open optical sample cell; and
    a detector for detecting light from the chirped laser that has passed through the open optical sample cell, wherein the open optical sample cell is defined by a mirror at each end, the mirrors being included in the vertical support, so that the open optical sample cell extends along the vertical support.

2. A portal or gateway as claimed in claim 1 wherein the open optical sample cell extends along substantially the full length of the vertical support.

3. A portal or gateway as claimed in claim 1 wherein the open optical sample cell is longer than approximately 1 meter.

4. A portal or gateway as claimed in claim 1, wherein the open optical sample cell is non-resonant.

5. A portal or gateway as claimed in claim 1 wherein the open optical sample cell is arranged so that light makes multiple passes through the open optical sample cell.

6. A portal or gateway as claimed in claim 1 further comprising means for directing gas in the portal towards the open optical sample cell.

7. A system comprising a plurality of portals or gateways, wherein at least one of the plurality of portals or gateways is defined as in claim 1.

8. A portal or gateway as claimed in claim 1 wherein the chirped laser comprises a semiconductor laser.

9. A portal or gateway as claimed in claim 5 wherein the open optical sample cell is arranged so that light makes one hundred or more passes through the open optical sample cell.

10. A portal or gateway as claimed in claim 6 wherein the means for directing gas comprise one or more fans.

11. A system as claimed in claim 7 wherein the plurality of portals or gateways share a single detector.

12. A system as claimed in claim 11 wherein light from the plurality of portals or gateways is passed to the single detector using fiber optic cable.

13. A portal or gateway as claimed in claim 8 wherein the light is generated by applying one or more substantially step function electrical pulses to the semiconductor laser to cause the semiconductor laser to output one or more light pulses for injecting into the open optical sample cell, wherein each of the one or more light pulses comprises a continuous wavelength chirp.

14. A portal or gateway as claimed in claim 13 wherein each of the one or more light pulses has a duration that is greater than approximately 150 ns.

15. A portal or gateway as claimed in claim 13 wherein each of the one or more light pulses has a duration that is in the range of approximately 150 to 300 ns.

16. A portal or gateway as claimed in claim 13 wherein a chirp rate of the one or more light pulses is selected so that there is a time delay between spots on reflecting elements of the open optical sample cell sufficient to substantially prevent light interference from occurring, wherein the spots define locations at which at least one of the one or more light pulses is reflected from walls of the open optical sample cell.

17. A portal or gateway as claimed in claim 16 wherein each of the one or more light pulses has a duration that is greater than approximately 150 ns.

18. A portal or gateway as claimed in claim 16 wherein each of the one or more light pulses has a duration that is in the range of approximately 150 to 300 ns.

* * * * *

UNITED STATES PATENT AND TRADEMARK OFFICE
CERTIFICATE OF CORRECTION

PATENT NO. : 8,339,606 B2  
APPLICATION NO. : 12/516947  
DATED : December 25, 2012  
INVENTOR(S) : Iain Howieson Page 1 of 1

It is certified that error appears in the above-identified patent and that said Letters Patent is hereby corrected as shown below:

Title Page Item (30) change foreign application priority data "0623812.5" to read as follows:

---0622812.5---

Signed and Sealed this  
Seventh Day of May, 2013

Teresa Stanek Rea  
*Acting Director of the United States Patent and Trademark Office*